United States Patent [19]

Lahr

[11] Patent Number: 5,005,586

[45] Date of Patent: Apr. 9, 1991

[54] METHOD FOR EXERCISING A PATIENT'S ANAL CANAL

[76] Inventor: Christopher J. Lahr, 103 Rutledge Ave., Charleston, S.C. 29401

[21] Appl. No.: 337,200

[22] Filed: Apr. 14, 1989

Related U.S. Application Data

[60] Continuation-in-part of Ser. No. 174,203, Mar. 28, 1988, abandoned, which is a continuation-in-part of Ser. No. 51,636, May 20, 1987, Pat. No. 4,739,767, which is a division of Ser. No. 836,729, Mar. 6, 1988, Pat. No. 4,687,002.

[51] Int. Cl.⁵ .............................................. A61B 5/10
[52] U.S. Cl. .................................... 128/774; 128/898; 606/192; 606/197
[58] Field of Search ...................... 128/344, 348.1, 774, 128/778, 782, 898; 606/192, 197; 604/96–103

[56] References Cited

U.S. PATENT DOCUMENTS 2,541,520  2/1951  Kogel ................................. 606/192

Primary Examiner—Randall L. Green
Assistant Examiner—Randy Shay
Attorney, Agent, or Firm—Senniger, Powers, Leavitt and Roedel

[57] ABSTRACT

A sphincterogram device used with radiographic equipment for measuring a patient's anal canal length, anal canal pressure, anorectal angle, and fatigability of the anal musculature. The sphincterogram device comprises an elongated expandable balloon having a flexible tubular catheter disposed substantially therein. The balloon is adapted for insertion into the patient's anal canal. The catheter has a plurality of openings spaced along a substantial portion of its length for communicating between the interior of the balloon and the interior of the catheter. The sphincterogram device also includes at least one fluid supply reservoir and at least one fluid flow line interconnecting the reservoir and the balloon for flow of fluid therebetween. The fluid supply reservoir is adapted for adjusting fluid pressure therein and for adjusting fluid pressure and volume in the catheter and balloon, and calibrations are provided for determining fluid pressure within the balloon. Additional aspects of this invention include a two reservoir system having two one way valves for exercising an anal sphincter; a method for measuring anal canal length, anal canal pressure, anorectal angle, and fatigability of the anal musculature; and a method for exercising the anal sphincter.

4 Claims, 5 Drawing Sheets

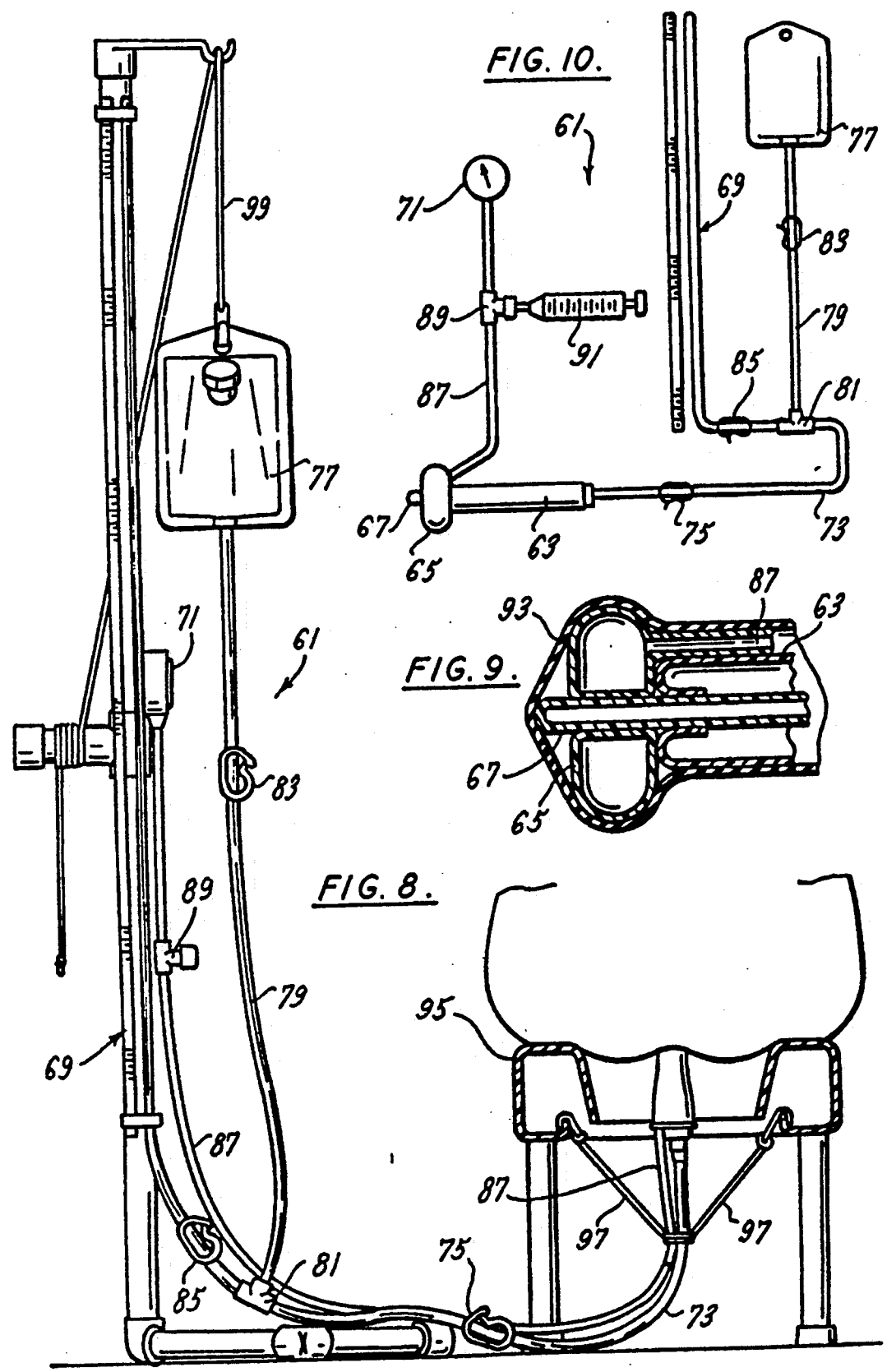

METHOD FOR EXERCISING A PATIENT'S ANAL CANAL

This application is a continuation-in-part and divisional application of Application Ser. No. 174,203, abandoned, which in turn was a continuation-in-part and divisional application of Application Ser. No. 051,636, now U.S. Pat. No. 4,739,767, which in turn was a divisional application of Application Ser. No. 836,729, now U.S. Pat. No. 4,687,002.

BACKGROUND OF THE INVENTION

This invention relates to sphincterograms, and more particularly to a hydraulic sphincterogram device and a sphincterography method which is especially adapted for use in diagnosis of anal dysfunction, such as anal incontinence and rectal prolapse, the sphincterogram device also being adapted for use as an anal sphincter exerciser.

Anal incontinence (the inadvertent release of rectal contents due to failure of the anorectal/pelvic musculature) and rectal prolapse (the protrusion of the rectum through the anus) are common, embarrassing and, not surprisingly, under-diagnosed problems. It has been suggested that two distinct muscular mechanisms maintain fecal continence: (1) squeeze of the muscle fibers of the anal sphincter closes the anal canal lumen, and (2) contraction of the puborectalis levator ani muscles flattens the distal rectum horizontally and kinks it at the anorectal angle thereby preventing transmission of intra-abdominal pressure into the anal canal. Anal incontinence may be associated with short anal canal length, low anal squeeze pressures and a wide (flat) anorectal angle. Rectal prolapse may be associated with a flat anorectal angle with or without low squeeze pressures.

Radiographic studies have been developed which allow actual visualization of the anal canal and measurement of the anorectal angle. These studies have heretofore been tedious, time consuming, unpleasant and messy. For example, S. Phillips and D. Edwards, *Some Aspects of Anal Continence and Defaecation*, 6 Gut 396-406 (1965), disclosed a method for determining the shape and position of the anal canal during defecation with cineradiography after coating the mucosa of the anal canal with barium sulfate powder. Barium soaked swabs, metal beaded chains, and various consistencies of barium have also been used to determine the anorectal angle.

The use of a balloon proctogram has been suggested as a tool for diagnosis of anal function. For example, Preston, Lennard-Jones and Thomas, *The Balloon Proctogram*, 71 Br. J. Surg. 29 (1984), discloses a barium filled balloon used to simulate a soft stool. After insertion and inflation of the balloon, a patient sits on a radiolucent lavatory seat. While the patient is sitting, the level of the pelvic floor, change of the anorectal angle and behavior of the anal sphincters during straining and defecation are visually demonstrated with lateral radiographs.

While the simplicity and cleanliness of this barium filled balloon is desirable, the particular design described above is disadvatageous in that it does not provide for measurement of anal canal (sphincter) pressure and fatigability of the anal musculature. The other methods outlined above, in addition to being unpleasant and messy, share this disadvantage. Therefore, one distinct muscular mechanism for maintaining anal contingence has been ignored by these approaches to diagnosis of anal incontinence.

Also, these techniques do not provide for exercise of the anal sphincter, which may be a promising treatment for some forms of anal dysfunction, such as anal incontinence. "Anal aerobics", however, is not part of the traditional treatment of anal incontinence. An exercise for strengthening the anal musculature should include repeated relaxation and contraction of the anal sphincter. By definition, contraction must be against pressure that is below the maximum anal canal squeeze pressure and above the opening pressure of the resting anal sphincter. Any apparatus and method for exercising the anal musculature should be easy to use and designed to prevent excessive strain and internal injuries. Ideally, an apparatus and method for anal exercises should be capable of determining anal function, and an apparatus and method for determining anal function should be capable of exercising the anal musculature.

SUMMARY OF THE INVENTION

Among the several objects of this invention may be noted the provision of a sphincterogram device and sphincterography method which are safe, reliable, easy and not unpleasant to use, and which measures a patient's anal canal length, anal canal pressure, anorectal angle, fatigability of the anal musculature and the like. Also, some other objects of this invention are the provision of a sphincter exercising apparatus and method that is safe, reliable and easy to use. Another object of this invention is the provision of a sphincterogram that is capable of use for sphincter exercising.

Generally, a sphincterogram device of the Present invention is used with radiographic equipment for measuring a patient's anal canal length, anal canal pressure, anorectal angle, and fatigability of the anal musculature. It comprises an elongated expandable balloon having a flexible tubular catheter disposed substantially therein. The balloon is adapted for insertion into the patient's anal canal. The catheter has multiple openings spaced along a substantial portion of its length for communicating between the interior of the balloon and the interior of the catheter. The sphincterogram device also includes at least one fluid supply reservoir and at least one fluid flow line interconnecting the reservoir and the balloon for flow of fluid between them. Pressurizing means is operable on the fluid supply reservoir for adjusting fluid pressure therein and for adjusting fluid pressure and volume in the catheter and balloon, and calibration means is associated with the pressurizing means for determining fluid pressure within the balloon. In other words, raising the fluid reservoir increases the pressure inside the sphincterogram balloon and measuring the elevation of the reservoir above the balloon allows the user to calculate pressure within the balloon.

In a second aspect of this invention, the apparatus, which also constitutes an anal sphincter exerciser, comprises an elongated expandable balloon having a flexible tubular catheter disposed substantially therein. The balloon is adapted for insertion into the patient's anal canal. The catheter has a plurality of openings spaced along a substantial portion of its length for communicating between the interior of the balloon and the interior of the catheter. The exerciser also includes a fluid supply reservoir and a fluid retention reservoir. The fluid supply reservoir communicates with the catheter and balloon through a first fluid flow line, one end of which is connected to the balloon and the other end of which is connected to the fluid supply reservoir. The fluid retention reservoir communicates with the catheter and balloon through a second fluid flow line, one end of which is connected to the balloon and the other end of which is connected to the fluid retention reservoir. Fluid is contained within the balloon, catheter, first fluid flow line, fluid supply reservoir, second fluid flow line and fluid retention reservoir. The first fluid flow line has a first one way valve therein, which allows fluid flow toward the balloon and prevents fluid flow toward the fluid supply reservoir, and the second fluid flow line has a second one way valve therein, which allows fluid flow away from the balloon and prevents fluid flow away from the fluid retention reservoir. This arrangement causes minimum fluid pressure within the balloon to be dependent on the pressure at the fluid supply reservoir side of the first one way valve and maximum fluid pressure within the balloon to be dependent on the fluid pressure required for fluid flow into the fluid retention reservoir. First means is operable on the fluid supply reservoir for varying the elevation of the fluid supply reservoir, which varies the fluid pressure at the reservoir side of the first one way valve, thereby adjusting the minimum fluid pressure within the balloon. Second means is operable on the fluid retention reservoir for varying the elevation of the fluid retention reservoir, which varies the fluid pressure required for fluid flow into the fluid retention reservoir, thereby adjusting the maximum fluid pressure within the balloon.

In a third aspect of this invention the apparatus constitutes an anal exercising device for exercising a patient's anal sphincter and abdominal muscles. It comprises first and second expandable balloons adapted for insertion into the patient's anal canal. A flexible tubular catheter is disposed substantially within the first balloon and has a plurality of openings spaced along a substantial portion of its length for communicating between the interior of the first balloon and the interior of the catheter. First and second pressure measuring devices are coupled to the first and second balloons, respectively. The first pressure measuring device is adapted to measure the pressure in the catheter within the first balloon. The second pressure measuring device is adapted to measure the pressure in the second balloon.

Also disclosed are methods for exercising the anal musculature and measuring various aspects of anal function, such as anal canal length, anal canal pressure, anorectal angle, and fatigability of the anal musculature.

Other objects and features will be in part apparent and in part pointed out hereinafter.

BRIEF DESCRIPTION OF THE DRAWINGS

FIG. 8 is a side elevation similar to FIG. 7 showing first and second balloons being used as an anal exerciser for a patient, including first and second pressure monitors for the patient to monitor the pressure exerted on the two balloons;

FIG. 9 is a cross-sectional view of the distal end of the anal exerciser of FIG. 8 showing the first and second balloons; and FIG. 10 is schematic of the anal exerciser of FIG. 8.

Corresponding reference characters indicate corresponding parts throughout the several views of the drawings.

DESCRIPTION OF PREFERRED EMBODIMENTS

Figure 1:
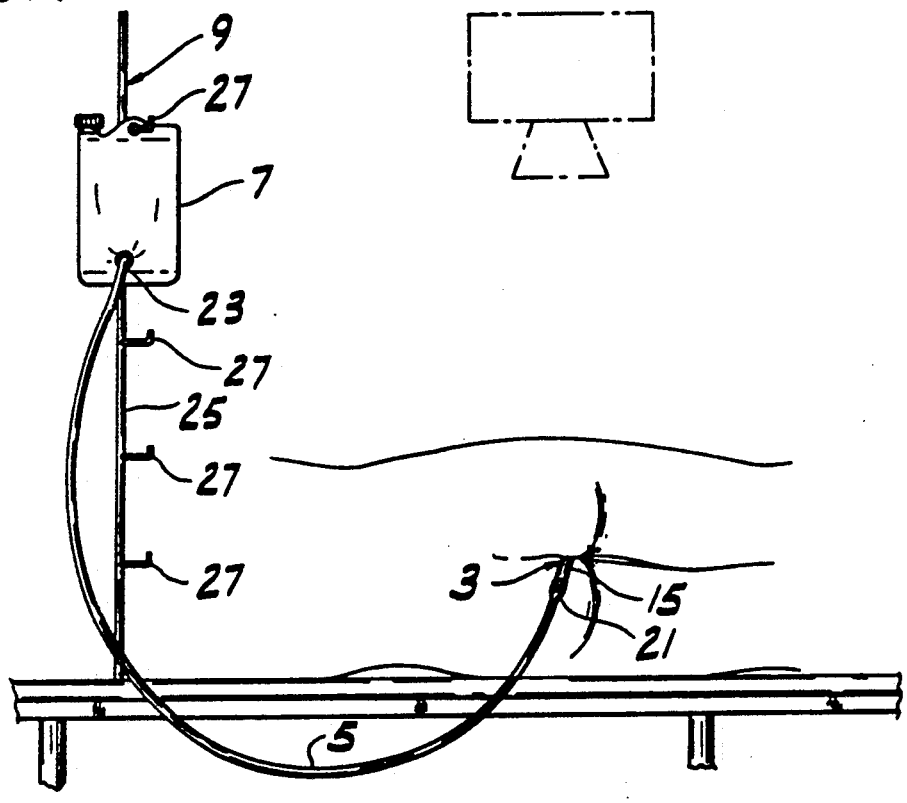
FIG. 1 is a side elevation of a sphincterogram device of the present invention illustrating a patient receiving a sphincterogram.

Referring to the drawings, a sphincterogram device of the present invention is designated in its entirety by the reference numeral 1. As shown in FIG. 1, the sphincterogram device comprises a balloon catheter 3, at least one fluid flow line 5 (or first fluid flow line), and fluid supply reservoir 7. The fluid supply reservoir may be suspended by a first stand 9. Preferably, radiopaque fluid 11 is contained within the balloon catheter 3, first flow line 5, and fluid supply reservoir 7. For example, low viscosity radiographic contrast, sold under the trade designation "Cystograffin", may be used.

Figure 2:
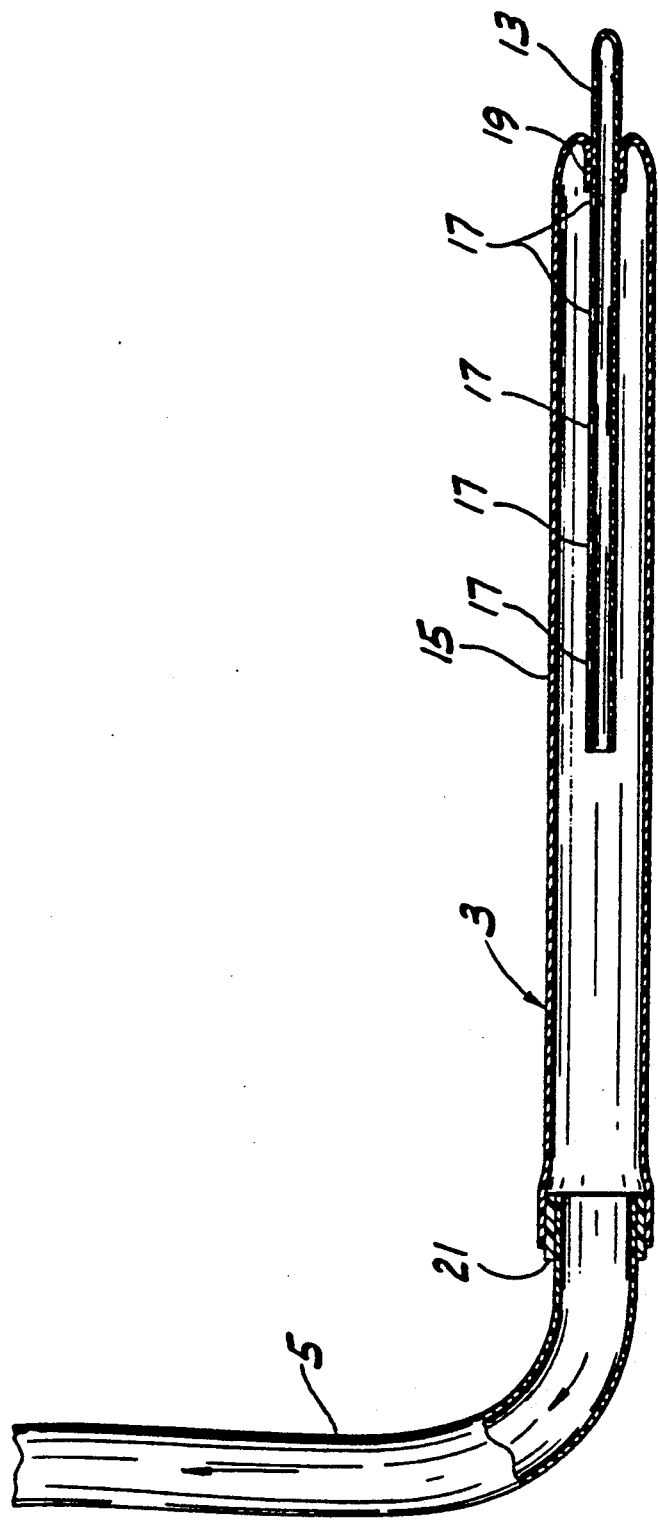
FIG. 2 is a side view, partly in cross section, of a balloon catheter for the sphincterogram device of FIG. 1.

As shown in FIG. 2, the balloon catheter 3 comprises an elongate catheter 13 and an elongated expandable balloon 15. The catheter 13 may be relatively flexible (e.g., of rubber) so as to bend with the contour of an anal canal and rectum, but firm enough to be inserted in the anal canal. It may be tubular (hollow) and have a plurality of openings or perforations 17 spaced along a substantial portion of its length. These perforations facilitate fluid movement within the balloon catheter 3 even when a section or sections of the balloon are collapsed. This maintains an even fluid pressure throughout the balloon during use. Preferably, the catheter is a 16 French catheter having a 20 cm length, and the perforations have a 5 mm diameter.

The balloon 15 may be constructed of a one inch (25 mm) Penrose drain, having an unstretched circumference of 3.14 inches (80 mm). It may be attached to the catheter at 19 by any suitable method of attachment and sealing. The balloon preferably has a length of 30 cm from the attachment area 19 to one end 21 of the first fluid flow line 5, which is where the balloon catheter is connected to the first fluid line. Any suitable method of attachment to the first line 5 that is strong and prevents leaking should be acceptable. The first line may be a large diameter flexible tube (having e.g., a ⅝ inch (16 mm) lumenal diameter).

As shown in FIG. 1, the other end 23 of the first fluid line is connected to the fluid supply reservoir 7, so that the fluid supply reservoir 7 may communicate with the balloon catheter 3 through the first fluid flow line 5. Thus, the radiopaque fluid may move or flow through the first line between the fluid supply reservoir and the balloon catheter. The elevation of the fluid supply reservoir 7 may be varied by moving it along an upright member 25 of first stand 9. An increasing elevation of the fluid supply reservoir 7 relative to the balloon catheter 3 causes increasing fluid pressure and possibly increasing fluid volume within the balloon catheter. Also, any relative elevation of the fluid supply reservoir corresponds to a specific fluid pressure within the balloon catheter. The stand 9 constitutes pressurizing means operable on the fluid supply reservoir 7 and first means operable on the fluid supply reservoir for adjusting fluid pressure within the balloon catheter 3 whereby fluid pressure within the balloon catheter are varied.

The upright member 25 of the first stand may be marked at constant intervals so as to calibrate the stand for easier determination of the first reservoir's elevation relative to the balloon catheter. Alternatively, hooks 27 may be at constant intervals along the upright member 25 for the same purpose. Therefore, marks, hooks 27 or the like constitute first calibration means for determining fluid pressure within the balloon catheter.

The fluid supply reservoir 7 may be, for example, an ordinary enema bag. Preferably, it has a large volume relative to the balloon catheter 3. Because of this large relative volume, any change of the volume of the balloon catheter causes only a small change in the elevation of the fluid within the fluid reservoir. Since the elevation of the fluid is only minimally affected by the balloon catheter's shape and size, the fluid pressure within the balloon catheter is only minimally affected by such changes in shape and size. This feature of stable pressure permits accurate measurement of sphincter pressure.

Figure 3:
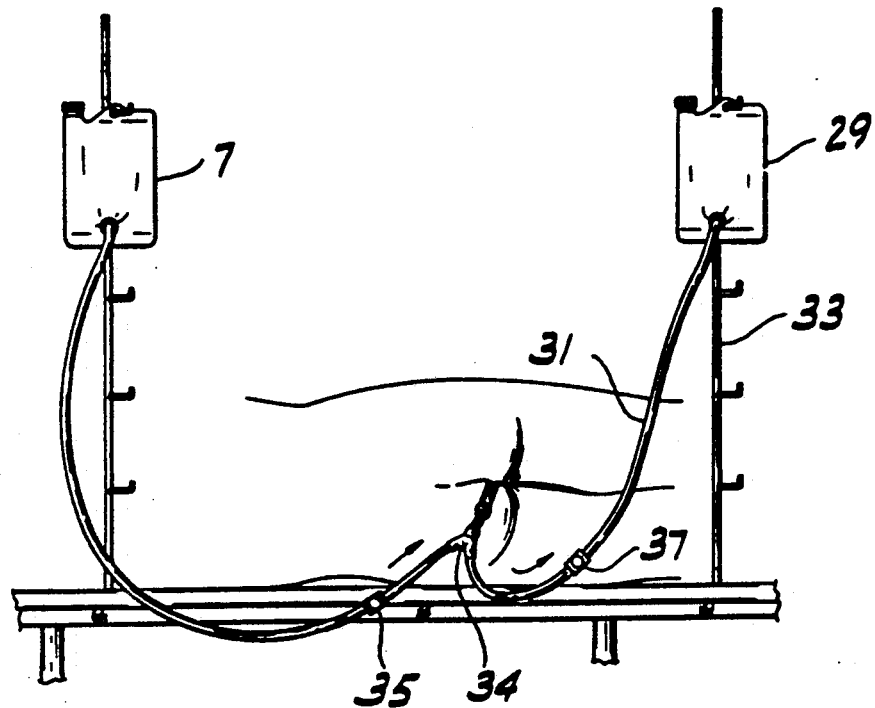
FIG. 3 is a side elevation similar to FIG. 1 showing use of the sphincterogram device as a sphincter exerciser.

Referring to FIG. 3, a second embodiment of the present invention can be utilized as an anal sphincter exerciser, which is generally designated in its entirety by the reference numeral 29. The exerciser comprises a fluid retention reservoir 29, an additional (or second) fluid flow line 31, and a second stand 33 in addition to the features of the sphincterogram device. The fluid retention reservoir 29 may be of identical construction as the fluid supply reservoir 7. However, the exerciser does not require radiopaque fluid unless it is also being used to obtain a sphincterogram. If the exerciser is being used solely for exercise of the anal sphincter, it only requires a suitable fluid for that use.

Instead of directly connecting the first and second fluid flow lines to the balloon catheter 3, a Y-connector 34 may be used. The first fluid flow line 5 may have a first one way valve 35 therein, and the second fluid flow line 31 maY have a second one way valve 37 therein. The first valve 35 allows fluid flow toward the balloon catheter 3 and prevents fluid flow toward the fluid supply reservoir 7, while the second valve 37 allows fluid flow away from the balloon catheter 3 and prevents fluid flow away from the fluid retention reservoir 29. This arrangement causes (1) the minimum possible fluid pressure within the balloon catheter 3 to be dependent on the pressure at the fluid supply reservoir side of the first one way valve 35, and (2) the maximum possible fluid pressure within the balloon catheter 3 to be dependent on the fluid pressure required for fluid flow into the fluid retention reservoir 29. It is understood that the first fluid flow line 5 may only have a one way valve when more than one fluid reservoir is attached (e.g., fluid supply reservoir 7 and fluid retention reservoir 29). Otherwise, fluid may not be able to escape from the balloon.

Therefore, the first stand 9 constitutes first means operating on the fluid supply reservoir 7 for varying the elevation of the fluid supply reservoir whereby the minimum fluid pressure within the balloon catheter 3 is controlled by varying the fluid pressure at the fluid supply reservoir side of the first one way valve 35. The second stand 33 constitutes second means operable on the fluid retention reservoir 29 for varying the elevation of the fluid retention reservoir whereby the maximum fluid pressure within the balloon catheter 3 is controlled by varying the fluid pressure required for fluid flow into the fluid retention reservoir.

It is not necessary to use the two reservoir embodiment to perform diagnostic radiographic studies. To perform sphincterography, a patient may be placed, left side down, on a fluoroscopy table 39. Then approximately six inches (150 mm) of the deflated (and lubricated) balloon catheter 3 may be placed in the anal canal and distal rectum. Fluoroscopy may be utilized to visually demonstrate the patient's anal function. (Fluoroscopy is used herein as any method to produce a continuous X-ray picture or the like; radiography means any method to produce an X-ray picture and the like, including fluoroscopy.) Various measurements relevant to anal function may then be made.

First, the fluid supply reservoir 7 may be raised in increments, so that the fluid pressure within the balloon 15 is raised in increments until it is seen to open the resting anal canal. The pressure may be calculated by multiplying the fluid supply reservoir's height relative to the balloon by the density of the radiopaque fluid relative to water. In this case, the result is the opening pressure of the anal sphincter in centimeters of water.

Second, to determine the patient's maximum anal canal squeeze, the patient may voluntarily squeeze his anal sphincter against low balloon pressure, so that the balloon collapses. Then the pressure within the balloon may be raised in increments until the patient is unable to collapse it with his squeeze. The maximum anal canal squeeze pressure is the highest pressure at which the patient is able to collapse the balloon within the anal canal. Permanent single full-size radiographs may be taken during initial maximum squeeze at balloon pressures of 20 cm $H_2O$, 40 cm $H_2O$, 60 cm $H_2O$, and 80 cm $H_2O$ for easy measurement and documentation.

Figure 4:
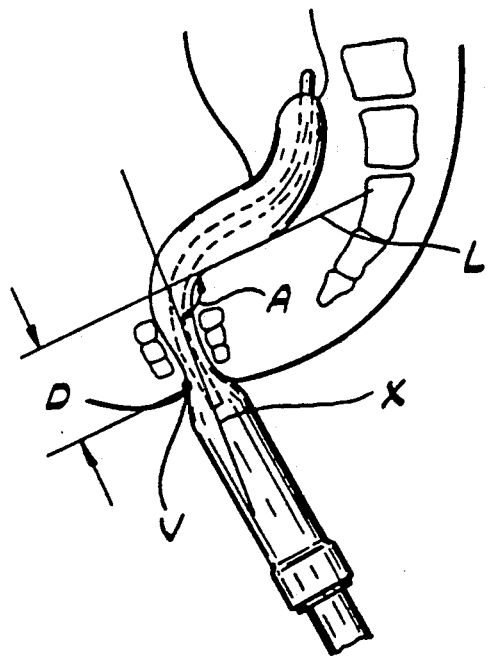
FIG. 4 is a side view of a normal subject's rectal region, showing an anorectal angle and anal canal length.
Figure 5:
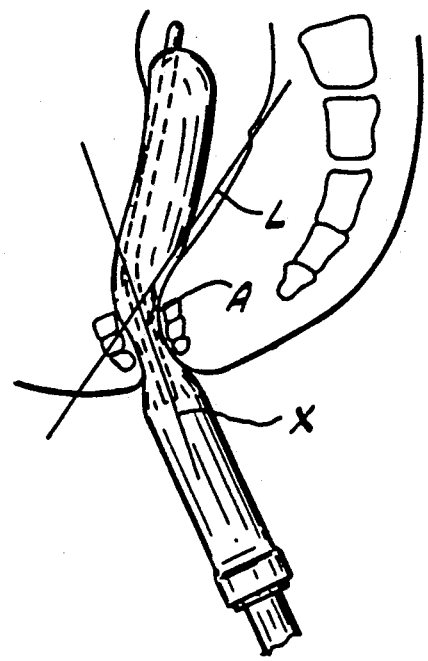
FIG. 5 is a side view, similar to FIG. 4, of the rectal region of a patient suffering from rectal prolapse.
Figure 6:
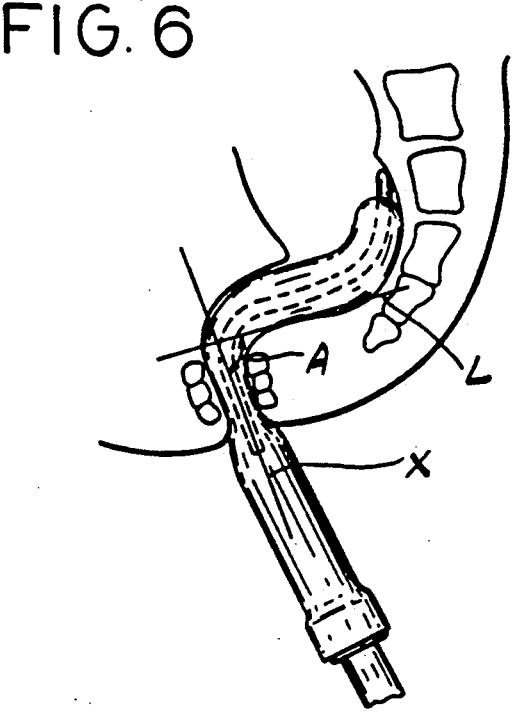
FIG. 6 is a side view, similar to FIG. 4, of the rectal region of a patient suffering from chronic constipation.

As shown in FIGS. 4–6, the anorectal angle A is the angle between the axis of the anal canal X and the rectal ledge L. It may be measured at any time during sphincterography, but a preferred standard procedure for accurate comparisons between patients is to measure the angle during initial voluntary anal squeeze with a balloon pressure of 40 cm water. Also, the length of the anal canal (the distance D between the rectal ledge L and the anal verge V) may be measured at this time.

The anorectal angle A is normally approximately 100-110 degrees, as shown in FIG. 4. If the patient has prolapse or anal incontinence the angle A may be relatively flat (e.g., approximately 130 degrees), as shown in FIG. 5. A patient suffering from chronic constipation may have a relatively small anorectal angle A (e.g., approximately 90 degrees), as shown in FIG. 6.

The sphincterogram device may also be used to exercise a patient's anal sphincter when both fluid reservoirs are connected. Preferably, the fluid supply reservoir 7 is filled with fluid and the fluid retention reservoir 29 is empty. The balloon catheter 3 is placed inside the anal canal. Then the fluid retention reservoir 29 may be raised to an elevation below that which obtains the maximum squeeze pressure within the balloon. Next, the fluid supply reservoir 7 may be raised until the opening pressure of the anal canal is obtained within the balloon 15. This is the precise pressure sufficient to inflate the balloon while the sphincter is relaxed. It is also the minimum possible fluid pressure within the balloon catheter 3 during the exercises. The sphincterogram device is now ready for the patient to begin the exercises.

The patient may exercise the anal sphincter by voluntarily contracting his or her anal sphincter, thereby forcing fluid out of the balloon 15 into the fluid retention reservoir 29. The higher the elevation of the fluid retention reservoir 29, the greater the pressure the sphincter must generate to compress the balloon and, thereby, force fluid into the fluid retention reservoir 29. After the patient has compressed the balloon, he or she may relax his or her sphincter, allowing the balloon to fill up again with fluid from the fluid supply reservoir 7. The balloon is now ready for another compression. This process may be repeated until the fluid supply reservoir is empty.

Figure 7:
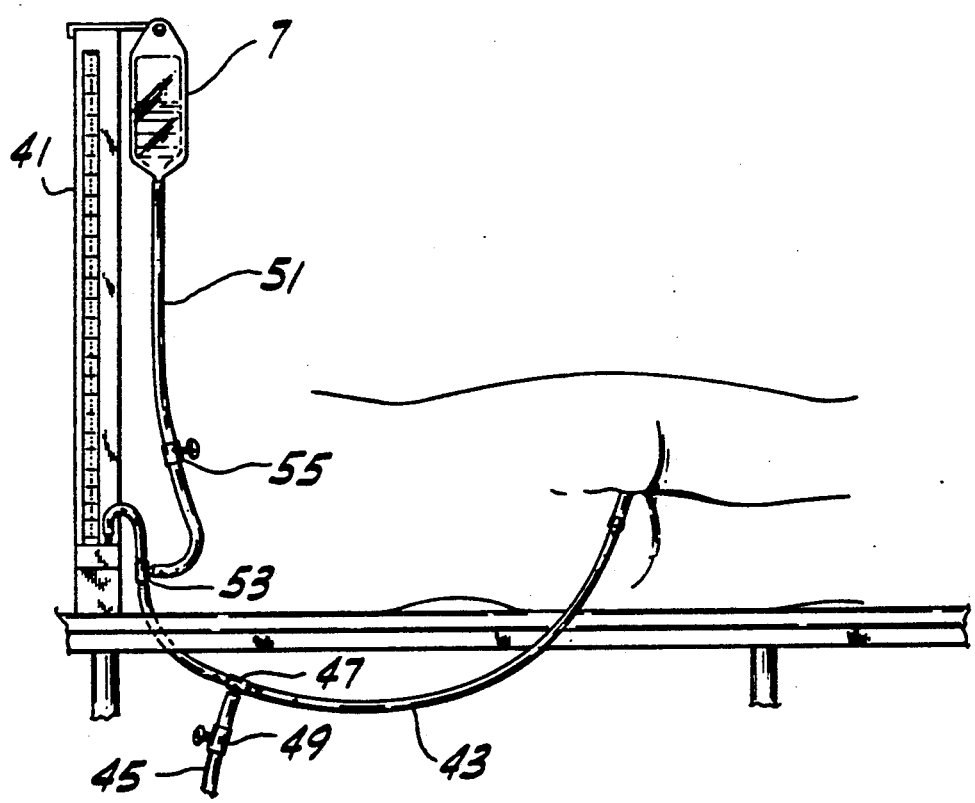
FIG. 7 is a side elevation similar to FIG. 3 showing use of the sphincterogram device as a sphincter exerciser, including a pressure monitor for the patient to monitor the pressure exerted.

FIG. 7 shows an alternate embodiment of an anal exercise device constructed according to the principles of this invention, in which the anal exercise device of the present invention is connected to a manometer 41 or some other suitable pressure measuring and display device rather than to the fluid retention reservoir 29. The balloon catheter (not shown in FIG. 7) is placed inside the anal canal. The balloon catheter is connected via line 43 to the manometer 41. A drain tube 45 is connected to line 43 with a T-shaped fitting 47. The drain is closeable with a valve 49. The fluid supply reservoir 7 is connected to fluid supply line 51. The line 51 is connected to line 43 with T-shaped fitting 53. The fluid supply line 51 is closeable with valve 55. The valve 55 is opened to fill the catheter 3 in the anal canal with fluid, and establish a preselected base pressure in the manometer 41. When the preselected pressure is reached, the valve 55 is closed. The manometer 41 is placed where the patient can observe it. The patient is then directed to tighten and relax his or her anal sphincter. As the patient tightens his or her sphincter, the fluid level in the manometer increases, and as the patient relaxes his or her sphincter the fluid level falls. By observing the fluid level in the manometer the patient can learn to control the anal sphincter. This bio-feedback training helps the patient strengthen the sphincter or learn to voluntarily relax it.

When the training session is over, valve 49 can be used to drain the system, so that the catheter can be removed from the patient's anal canal.

FIGS. 9-11 show an alternate embodiment of an anal exercise device, designated generally at 61, constructed according to the principles of this invention, in which two balloons are connected to two pressure measuring devices. It has first and second balloons 63 and 65 adapted for being inserted into the anal canal of a patient. The first balloon 63, similar to the balloon catheter 3 of FIG. 2, is used to measure sphincter pressure. The second balloon 65 is a ring-shaped balloon which fits over an elongate catheter 67 of the first balloon 63 and is disposed adjacent the first balloon 63. The second balloon 65 is used to measure abdominal pressure.

The first balloon 63 is connected to a manometer 69 or some other suitable pressure measuring and display device. The second balloon 65 is connected to an aneroid pressure meter 71 or some other suitable pressure measuring and displaY device. The manometer 69 constitutes a first pressure measuring device and the aneroid pressure meter 71 constitutes a second pressure measuring device. The first balloon 63 is connected via line 73 to the manometer 69. The line 73 is closeable with a clamp 75. A fluid supply reservoir 77 is connected to a fluid supply line 79. The line 79 is connected to line 73 with a T-shaped fitting 81. The fluid supply line 79 is closeable with a clamp 83. The clamp 83 constitutes stop means for interrupting fluid communication between the reservoir 77 and the catheter 67. The manometer 69 is closeable with a clamp 85. The second balloon 65 is connected via line 87 to the aneroid pressure meter 71. An access port 89 is connected to line 87 so that fluid can be inserted into and/or removed from the second balloon 65 by a syringe 91 (shown in FIG. 10).

In operation, the balloons 63 and 65 are inserted in the anal canal of a patient. A protective sheath 93, such as an ordinary condom, is placed over the balloons 63 and 65 and lubricated with a water soluble lubricating gel prior to insertion. Preferably, the patient is seated on a training commode 95 during use of the exercise device 61. Cords 97, secured to the commode 95, hold the balloons in position within the patient's anal canal. The clamps 75 and 83 are loosened to fill the first balloon 63 with fluid and establish a preselected base pressure in the manometer 69. When the preselected pressure is reached, the clamps 75 and 83 are tightened. Fluid is injected by the syringe 91 through the port 89 and into the second balloon 65 to establish a preselected base pressure in the pressure meter 71. The manometer 69 and pressure meter 71 are placed where the patient can observe them. The patient is then directed to tighten and relax his or her anal sphincter and abdominal muscles. As the patient tightens his or her sphincter, the fluid level in the manometer 69 increases, and as the patient relaxes his or her sphincter the fluid level falls. Likewise, as the patient tightens his or her abdominal muscles the pressure measured by the pressure meter 71 increases, and as the patient relaxes his or her abdominal muscles the pressure measured by the pressure meter 71 decreases. By observing the pressures in the manometer 69 and pressure meter 71 the patient can learn to control the sphincter and abdominal muscles. This bio-feedback training helps the patient strengthen and control the anal musculature.

When the training session is over, the fluid supply reservoir 77 is lowered, via cord 99, to the level of the patients anal canal. This causes the fluid to drain from the first balloon 63. Once the fluid is drained from the first balloon 63, clamp 83 is closed. Also, the syringe 91 is used to evacuate fluid from the second balloon 65. After they are drained, the balloons 63 and 65 can be removed from the anal canal.

It will be observed from the foregoing that the sphincterogram devices and sphincterography methods of the present invention provide apparatus and methods for diagnosis of anal dysfunction and exercise of the anal musculature, which is easy and not unduly unpleasant to use, and which allows low exposure to radiation.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A method for exercising a patient's anal canal, comprising the following steps:

(a) inserting first and second balloons in the patient's relaxed anal canal;
(b) at least partially filling each balloon with fluid to preselected pressures;
(c) connecting the first balloon to a first pressure measuring device to measure the pressure in the first balloon and connecting the second balloon to a second pressure measuring device to measure the pressure in the second balloon; and
(d) repeatedly contracting the anal sphincter against the first balloon whereby the pressure measured by the first pressure measuring device is increased and relaxing the anal sphincter whereby the pressure measured by the first pressure measuring device is decreased, and repeatedly contracting the abdominal muscles whereby the pressure measured by the second pressure measuring device is increased and relaxing the abdominal muscles whereby the pressure measured by the second pressure measuring device is decreased.

2. The method according to claim 1 further comprising the step of displaying the pressures measured by the first and second pressure measuring devices so that the patient can learn to improve anal sphincter control and abdominal muscle control.

3. The method according to claim 1 wherein the first pressure measuring device is a manometer displaying the measured pressure to the patient as a fluid level.

4. The method according to claim 1 wherein the second pressure measuring device is an aneroid pressure measuring device.

* * * * *